United States Patent [19]

Imagawa et al.

[11] 4,423,726
[45] Jan. 3, 1984

[54] SAFETY DEVICE FOR LASER RAY GUIDE

[75] Inventors: Kyoshiro Imagawa; Shiro Sakuragi, both of Kyoto, Japan

[73] Assignee: Agency of Industrial Science & Technology, Tokyo, Japan

[21] Appl. No.: 313,195

[22] Filed: Oct. 20, 1981

[30] Foreign Application Priority Data

Nov. 4, 1980 [JP] Japan ................... 55-153737

[51] Int. Cl.³ ............................... A61B 17/36
[52] U.S. Cl. .................. 128/303.1; 128/395; 219/121 LZ
[58] Field of Search ............. 128/303.1, 395–398; 219/121 LA, 121 LB, 121 LZ

[56] References Cited

U.S. PATENT DOCUMENTS

| 3,524,046 | 8/1970 | Brouwer | 219/121 LA |
| 3,710,798 | 1/1973 | Bredemeier | 128/303.1 |
| 3,782,823 | 1/1974 | Kandorski | 219/121 LZ |
| 3,795,784 | 3/1973 | Moll et al. | 219/121 LB |
| 3,920,951 | 11/1975 | Choven et al. | 219/121 LB |

FOREIGN PATENT DOCUMENTS 2832847  2/1980  Fed. Rep. of Germany ... 128/303.1

Primary Examiner—Lee S. Cohen
Attorney, Agent, or Firm—Wenderoth, Lind & Ponack

[57] ABSTRACT

A safety device for a laser ray guide in which a laser ray-receiving element is installed on the input side of a lens of a laser ray guide including said lens, and troubles occurring in said laser ray guide can be detected by means of said laser ray-receiving element.

2 Claims, 6 Drawing Figures

SAFETY DEVICE FOR LASER RAY GUIDE

DESCRIPTION OF THE INVENTION (1) Field of the Invention

The present invention relates to a safety device for a laser ray guide of a laser surgical knife used in surgical operations on the human body.

(2) Description of the Prior Art

Laser ray guides of this type, in which reflection by mirrors or fiber optics are used, have previously been proposed. At present, such guides using fiber optics are used more frequently than the those using mirrors. However, the performance of fiber optics for laser rays is not very good yet and for this reason sometimes there have been troubles because practically usable fiber optics for transmitting power has not been developed yet. The main troubles come from the fact that the output end of the fiber optics is heated by the energy of the laser rays and is gradually evaporated. That is to say, the output power of laser rays must be decreased which will interfere with the surgical operations, or the laser ray guide will deteriorate because the material of the fiber optics will be evaporated from the output end, and moreover such substance will adhere to lenses near said output end. Because of this said output end is roughened and the absorption by lenses is increased. Although at present the detection of abnormal temperatures at the end of the fiber optics can be carried out, it is a heat conductive type of detection and for this reason it has a defect that the response is slow and consequently troubles will have occurred already when an alarm is given. Furthermore, it is a temperature-detection type operation and consequently it has a defect that only local troubles can be detected.

SUMMARY OF THE INVENTION

The object of the present invention is to provide a safety device for a laser ray guide which can instantly detect troubles in order to promptly take steps to prevent such troubles from continuing.

This object is achieved by the provision of a laser ray guide and safety device comprising: a laser ray guide having an input element, an output element, and laser ray transmission means between said input and output elements; a first laser ray-receiving element positioned for receiving rays reflected from the input side of said output element; and a second laser ray-receiving element positioned for receiving rays reflected from the input side of said input element, whereby when an abnormal signal is produced by said first laser ray-receiving element it indicates trouble in said transmission means or said output element, and when an abnormal signal is produced by said second laser ray-receiving element it indicates trouble in a source of laser rays supplied to said input element or in said input element.

DESCRIPTION OF THE PREFERRED EMBODIMENTS

Figure 1:
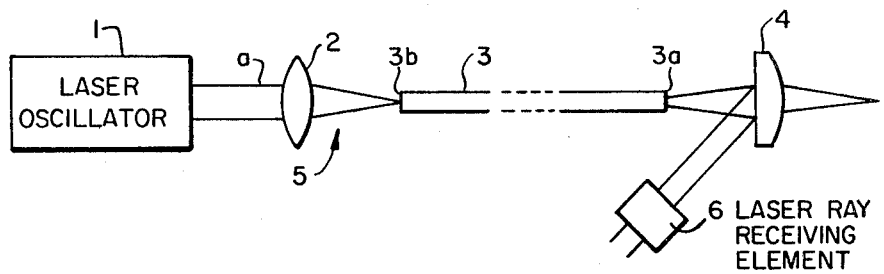
FIGS. 1 to 6 each show an example of a safety device for a laser ray guide according to the present invention.

Examples of the present invention will be described below by reference to the drawings. FIG. 1 shows a safety device for a laser ray guide according to one example of the present invention. Referring to FIG. 1, 1 designates a laser oscillator such as a $CO_2$ laser oscillator, and laser rays (a) emitted from said oscillator 1 are irradiated to the affected parts of the human body and the like after passing through a laser ray guide 5 consisting of lens 2, fiber optics 3 and lens 4. In FIGS. 1 to 6, the right side of said laser ray guide 5 from said lens 4 is called the output side while the left side of said laser ray guide 5 from said lens 4 is called the input side. 6 designates a laser ray-receiving element installed on the input side of said laser ray guide 5 for receiving rays reflected by said lens 4. Infrared ray detectors such as a thermopile, pyroelectric element or the like are used as said laser ray-receiving element 6.

If said output end 3a of said fiber optics 3 is heated by the energy of the laser rays in said laser ray guide 5 and evaporated substances adhere to the input side surface of said lens 4, the transmittance of said lens 4 is decreased and the output power of laser rays on the output side is decreased correspondingly. For this reason, the quantity of laser rays reflected by said lens 4 change at the same time. This change in the quantity of laser rays is detected by said laser ray-receiving element 6. Accordingly, the above described troubles at said output end 3a of said fiber optics 3 can be instantly detected by an operating surgeon or the like by connecting said laser ray-receiving element 6 with an alarm (not shown). In addition, said oscillator 1 can be made to stop its action the instant that said troubles occur so that they can be prevented from increasing by connecting said laser ray-receiving element 6 with said laser oscillator 1 instead of an alarm so that said laser oscillator 1 will stop its action the instant that a signal detected by said laser rays-receiving element 6 goes above the definite value. In such a construction, said laser ray-receiving element 6 receives laser rays reflected by said lens 4 and consequently said laser ray-receiving element 6 can detect all troubles occurring in said input side of said laser ray guide 5 from said laser oscillator 1 to said lens 4 including troubles at said lens 2 or said input end 3b of said fiber optics 3.

Figure 2:
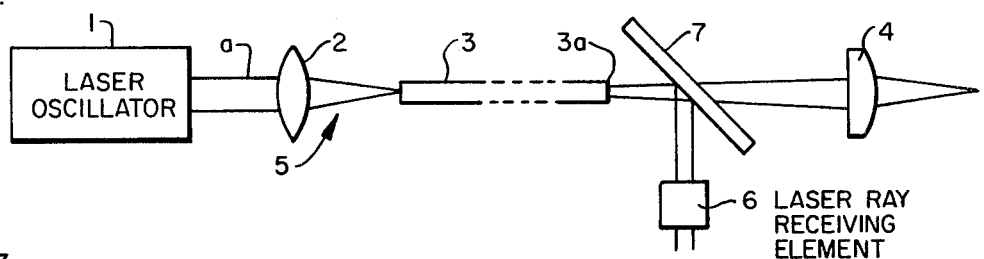

FIGS. 2 to 6 show other examples of the present invention, respectively. FIG. 2 shows a case in which a half mirror such as a 99% transmittal mirror 7 is installed in said laser ray guide 5 between said output end 3a of fiber optics and said lens 4, said laser ray-receiving element 6 being positioned so as to receive laser rays reflected by said mirror 7. The same infrared ray detector as described in the above-described example may be used as said laser ray-receiving element 6 because this example is similar to the above described example in respect of the manner in which said laser ray-receiving element 6 receives reflected laser rays. In this case, said laser ray-receiving element 6 can detect all troubles occurring in said laser ray guide 5 from said laser oscillator 1 to said half mirror 7.

Figure 3:
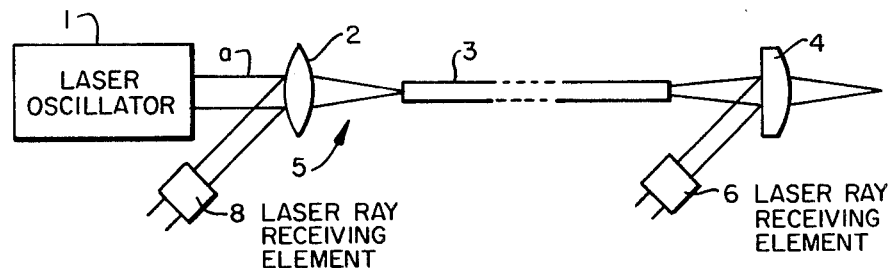

FIG. 3 shows an example in which a laser ray-receiving element 8 for receiving laser rays reflected by said lens 2 is provided in addition to said laser ray-receiving element 6 for receiving laser rays reflected by said lens 2 in order not only to detect troubles occurring in said laser ray guide 5 by means of said laser ray-receiving elements 6 and 8 but also to pinpoint the positions of those troubles. That is to say, if said laser ray-receiving element 8 is giving a regular detection signal while said laser ray-receiving element 6 produces an abnormal signal, the position of the trouble can be pinpointed as being in said fiber optics 3 or said lens 4. On the other hand, if both of said laser ray-receiving elements 6 and 8 give an abnormal signal, the position of the trouble can be pinpointed as being in said lens 2.

Figure 4:
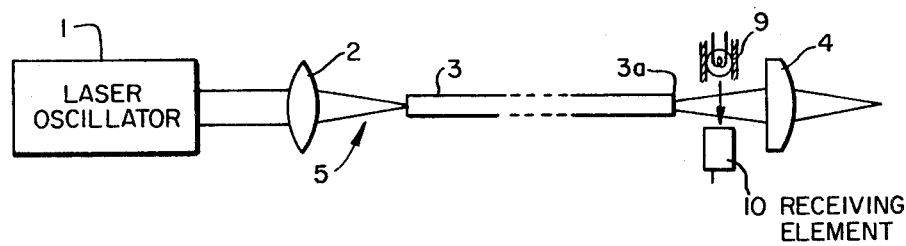

FIG. 4 shows an example in which a separate source of light 9 is installed near said laser ray guide 5, a laser ray-receiving element 10 receiving laser rays radiated from said source of light 9. In this construction, troubles occurring in said laser ray guide 5 are detected as follows. Substances evaporated from said output end 3a of the fiber optics due to heating adhere to the radiating surface of said source of light 9 installed near said laser ray guide 5 or to a light-receiving surface of said laser ray-receiving element 10. As a result, the detection signal of said laser ray-receiving element 10 is decreased in comparison with a situation in which there are no troubles. It is necessary to use an element responsive to light radiated from said source of light 9 as said laser ray-receiving element 10. Troubles, which can be detected by said laser ray-receiving element 10 are limited to those occurring near said source of light 9 and said laser ray-receiving element 10. Accordingly, the example shown in FIG. 4 is unsuitable for detecting all troubles occurring in said laser ray guide 5. However, this example also produces a speedy response and as a result can give an alarm the instant that troubles occur similarly to the other examples because this is also not a heat conductive type of detecting method.

Figure 5:
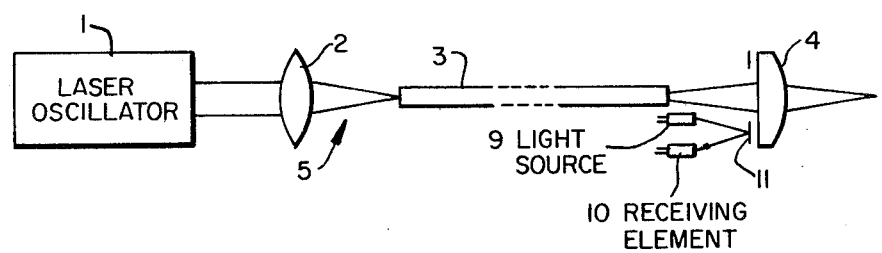

FIG. 5 shows an example in which said laser ray-receiving element 10 is positioned so that laser rays radiated from a source of light 9 will be reflected by a reflecting member 11 on said lens 4 and the resulting reflected light will be received by said laser ray-receiving element 10. Said reflecting member is constituted by, for example, a mirror surface on the part of said lens 4 on which laser rays from oscillator 1 do not fall. If evaporated substances adhere to said reflecting member 11, the quantity of reflected laser rays is decreased. Accordingly, such trouble can be detected by said laser ray-receiving element 10. Also in this example, trouble detectable by said laser rays-receiving element 10 is limited to that occurring near by said reflecting member 11 similarly to the example shown in FIG. 4.

Figure 6:
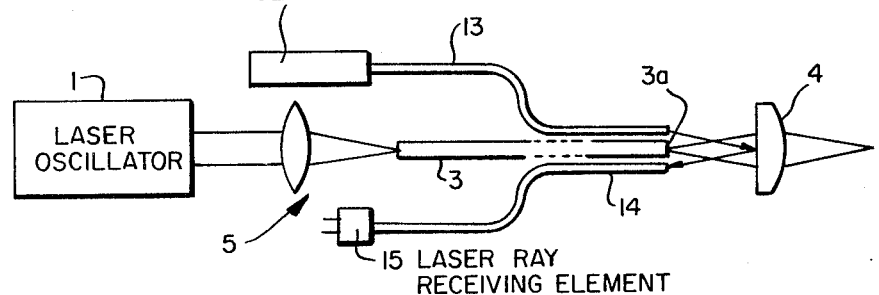

FIG. 6 shows an example in which a source of light 12 is provided which is a helium-neon laser, a radiation diode, a semiconductor laser or the like, laser rays radiated from said source of light 12 being guidied nearly to said output end 3a of said fiber optics 3 along said fiber optics 3 by means of fiber optics 13 and then applied to said lens 4, and laser rays reflected by said lens 4 being guided to a laser ray-receiving element 15 by means of fiber optics 14. The principle of detecting troubles is the same as in the example shown in FIG. 5.

Although in each of the above described examples a safety device consisting of laser ray-receiving elements and the like are used for a laser ray guide using fiber optics, the present invention is not limited to such a laser ray guide. It goes without saying that such a safety device consisting of laser ray-receiving elements and the like can be used with a laser rays guide of the mirror type.

As described above, a safety device for a laser ray guide according to the present invention is provided with a laser ray-receiving element or laser ray-receiving elements on an input side of a laser ray guide including a lens in order to detect troubles occurring in said laser ray guide by means of said element and consequently has the following effects:

(a) The safety device for a laser ray guide according to the present invention is different from the heat conductive type as described above because it uses an optical means and as a result can detect troubles instantly. Accordingly, an operating surgeon can be made aware of the occurrence of troubles by an alarm and at once take appropriate measures for preventing the troubles from continuing or growing worse by connecting a laser ray-receiving element with an alarm so that the alarm will be activated by a detection signal from the laser ray-receiving element. In addition, troubles can be automatically prevented from increasing by connecting the laser ray-receiving element with the laser oscillator so that the action of the laser oscillator will be stopped by a detection signal from the laser ray-receiving element. That is to say, appropriate measures can be taken instantly for preventing troubles from continuing because the occurrence of troubles can be detected by means of the laser ray-receiving element without delay.

(b) As indicated in the examples shown in FIGS. 1 to 3, all troubles occurring on the input side of the laser ray guide can be detected if laser rays are received by a laser ray-receiving element. That is to say, not only troubles occurring at an output end of the fiber optics but also troubles occurring in the total system including a source of light, lenses and the like can be detected.

(c) The output power of the laser rays can be always monitored on the basis of the detection signal of the laser ray-receiving element.

What is claimed is:

1. A laser ray guide and safety device comprising:
a laser ray guide having an input element, an output element, and laser ray transmission means between said input and output elements;
a first laser ray-receiving means positioned for receiving rays reflected from the input side of said output element and including means for producing an abnormal signal when the laser rays passing said output element are other than normal; and
a second laser ray-receiving means positioned for receiving rays reflected from the input side of said input element and including means for producing an abnormal signal when the laser rays passing said input element are other than normal, whereby when an abnormal signal is produced by said first laser ray-receiving means it indicates trouble in said transmission means or said output element, and when an abnormal signal is produced by said second laser ray-receiving means it indicates trouble in a source of laser rays supplied to said input element or in said input element.

2. A laser ray guide and safety device as claimed in claim 1 in which said input and output elements are input and output lenses, respectively.

* * * * *